United States Patent [19]

Bijlmer

[11] 4,072,896
[45] Feb. 7, 1978

[54] APPARATUS FOR MEASURING THE ELECTRON ESCAPE POTENTIAL OF METAL SURFACES

[75] Inventor: Paul Frederik Adriaan Bijlmer, Nieuw-Vennep, Netherlands

[73] Assignee: Fokker-VFW B.V., Schiphol-Oost, Netherlands

[21] Appl. No.: 699,204

[22] Filed: June 23, 1976

[30] Foreign Application Priority Data

June 23, 1975 Netherlands .......................... 7507475

[51] Int. Cl.$^2$ ............................................. G01R 27/26
[52] U.S. Cl. ................................. 324/61 P; 324/72; 324/109; 324/32
[58] Field of Search ................. 324/61 P, 61 R, 60 R, 324/60 C, 111, 109, 72, 32

[56] References Cited

U.S. PATENT DOCUMENTS

| 1,254,620 | 1/1918 | Newman | 324/111 |
| 3,379,972 | 4/1968 | Foster et al. | 324/61 P |
| 3,404,341 | 10/1968 | Young | 324/109 |
| 3,611,127 | 10/1971 | Vosteen | 324/72 |
| 3,772,592 | 11/1973 | Rhodes | 324/32 |

Primary Examiner—Stanley T. Krawczewicz
Assistant Examiner—Vincent J. Sunderdick
Attorney, Agent, or Firm—Snyder, Brown & Ramik

[57] ABSTRACT

An apparatus is disclosed for measuring the electron escape potential (or: Volta potential) of a metal surface. This apparatus comprises a conductive plate to be placed into the vicinity of and parallel to a metal surface under examination in order to form a capacitor; switch means for electrically connecting the conductive plate to a reference potential point; means for subjecting the conductive plate to vibration in a direction vertical to the metal surface; and an external circuit for measuring a measuring potential which is proportional to a current emitted by the capacitor. The conductive plate together with the switch means and part of the vibration-generating means are located in a probe and this probe is connected with the remainder of the apparatus by means of a flexible line which includes the required electric connections.

2 Claims, 2 Drawing Figures

APPARATUS FOR MEASURING THE ELECTRON ESCAPE POTENTIAL OF METAL SURFACES

This invention relates to apparatus for measuring the electron escape potential of metal surfaces and also to a probe for use in such apparatus.

It will be known that electrons may escape from metal surfaces under specific conditions. Such escape of electrons will require a certain amount of energy, however. If it is desired to remove an electron from the interior of a metal to the outside thereof, then it is necessary first to overcome the chemical potential of the electron in the interior of the metal and then to overcome a surface potential caused by double layers of electrostatic charges or oriented dipoles at the metal surface. The required escape energy or "real potential" may be calculated from these two potentials and will be called "electron escape potential" throughout this specification.

The electron escape potential may be measured by means of a method devised already by Kelvin and known as the "dynamic capacitor method". According to this method, a conductive plate is brought into close vicinity of the metal surface under examination in order to create a capacitor formed by such plate and such metal surface.

If an external electrical circuit is connected to such capacitor, a flow of electrons will pass through this circuit, and the electrochemical potentials of conductive plate and metal surface are equalised thereby. Nevertheless, an electrostatic potential difference is generated between the two surfaces and the value of this potential difference will be equal to the difference between the electron escape potentials of both surfaces.

Any variation in distance beween the conductive plate and the metal surface will cause a capacity variation in the capacitor. Since the electron escape potentials are independent from the capacitor plates spacing, such capacitor variation will be accompanied by a charge variation and will cause an electric current to flow through the external circuit. If the conductive plate is subjected now to periodic vibrations in a direction vertical to the metal surface under examination, this will result in an A.C. current flowing in the external circuit. The measuring potential generated in this external or measuring circuit is a standard for the electron escape potential since the A.C. current will satisfy the equation $i = dQ/dt = dC/dt \cdot V$ wherein: $i$ is the output A.C. current, $Q$ is the electric charge of the capacitor, $C$ is its capacitance and $V$ is the voltage across the capacitor.

Although, in principle, the dynamic capacitor method is suitable for measuring the electron escape potential, it is found to meet several difficulties in actual practice. A first difficulty is constituted by the conductive plate which, for measuring purposes, should be mounted at a correct distance and closely parallel to the metal surface under examination and which should also be capable of being displaced rapidly in order to allow measurements to be made at various spots of the metal surface. Another difficulty is constituted by the fact that the potential as measured has only a value of a few millivolts in most cases and this fact imposes limitations to the measuring method and increases the chances of errors. A third difficulty is that the measurement appears to be very sensitive to external disturbing influences such as mechanical and electrical vibrations.

Therefore, there is a need for a comparatively simple apparatus which may be mounted and displaced easily, which allows exact measurements to be made and which is insensitive to disturbing external influences.

An object of the invention is to satisfy this need.

The invention provides apparatus for measuring the electron escape potential of a metal surface which comprises the following elements: a conductive plate to be placed into the vicinity of and parallel to a metal surface under examination so as to form a capacitor; switch means for electrically connecting the conductive plate to a reference potential point; means for subjecting the conductive plate to vibration in a direction vertical to the metal surface; and an external circuit for measuring a measuring potential which is proportional to a current emitted by the capacitor. A special feature of this apparatus is that the conductive plate together with the electrical switch means and part of the vibration-generating means (i.e. the part engaging the plate) are located in a probe and that this probe is connected with the remainder of the apparatus (a measuring device) by means of a flexible line which includes the required electric connections as well. Thanks to this construction, a rapid mounting and rapid displacement of the conductive plate onto and over the metal surface under examination has become possible and the measurements may be carried out within a short time period.

The external circuit comprises preferably an electric compensation circuit located in the remaining part of the apparatus (i.e. outside the probe) and serving to introduce an opposite potential of equal but opposite value to the electron escape potential to be measured so as to cause the electrostatic potential difference between the surface of the conductive plate and the metal surface to become zero. A variation in distance between the two capacitor plates will cause no displacement of charges then, and a measurement according to the so-called "zero-method" becomes possible. The electron escape potential may be evaluated exactly then by measuring said opposite potential, i.e. the adjustable compensation potential. In connection therewith, it is advisable to use in the conductive plate a material having an electron escape potential of substantially constant value so as to obtain a good basis for comparison. As stated already before, the compensation circuit is located outside the probe.

The most important part of the apparatus is, of course, the probe, which comprises the conductive plate and accessories thereof such as the capacitor switch means, part of the vibration-generating means and, if desired, amplification means for the potential output. Preferably, the probe has a housing open to one side for surrounding all said accessories and carrying the conductive plate at its open side. Thus, the metal housing will form a Faraday cage which protects all parts therein effectively against external disturbing influences but which nevertheless permits a free operation of the plate.

The conductive plate should be capable of vibrating independently from the probe housing. To this end, the plate has been insulated mechanically and electrically with respect to the probe housing. In a preferred embodiment, the plate has been fixed to the membrane of a loudspeaker fitted within the housing but mechanically and electrically insulated from it, whilst a solenoid present in the loudspeaker forms part of the vibration means for the conductive plate. The latter plate may then be caused to vibrate by the solenoid of the loudspeaker through the membrane. In this way, a simple but efficient solution for the required vibration of the plate has been given.

If the probe is placed onto a surface to be measured, the conductive plate should attain a correct spacing from that surface and should extent parallel to it. For this purpose, the probe has been provided with spacers protruding from the face of the conductive plate but mechanically and electrically insultated from that plate. In a certain embodiment, these spacers may comprise extensions of the walls of the probe housing.

Furthermore, if the probe is placed onto the metal surface there should be a good electric contact between this metal surface and the capacitor switch means of the probe. Therefore, the probe has been provided with contact points for making electric contact with the metal surface to be measured. These contact points also protrude from the face of the conductive plate and have been insulated mechanically and electrically from that plate.

In a preferred embodiment, a combination of the two latter features is applied. In that embodiment, the contact points are spacers as well and are connected both mechanically and electrically to the housing. If the probe is placed then onto the metal surface, a correct position of the conductive plate and a good electric contact will always be ensured.

When using the apparatus described above and the probe belonging to this apparatus, the electron escape potential of a metal surface in relation to that of the conductive plate may be measured in a fast and efficient way.

Metal surfaces will develop an oxide coating at exposure to the air; in that case, the measurement relates to the system: conductive plate-intermediate surstance (if any)-oxide coating-metal. Further, the electron escape potential may be affected by adsorption of polar vapours such as $H_2O$ or $CO_2$. Therefore, the measurement may give an impression of the quality of the metal surface such as the presence of bare metal (in vacuo), or the presence of oxide layers, polar vapours, coatings, dust and dirt, and the like. Proceeding in this way, the measurements may be used for examining the quality of metal surfaces after being subjected to certain specific treatments (for instance aluminum surfaces which have been pickled with the aid of a chromic acid-sulfuric acid bath) and/or examining the quality of metal surfaces prior to being subjected to a certain specific treatment (for instance aluminum surfaces which have to be provided with an adhesive). The field of application is not restricted thereby, however, and the utilisations as mentioned above are given only as examples.

The invention will be further illustrated by the drawing which shows an embodiment of the invented apparatus by way of example.

Figure 1:
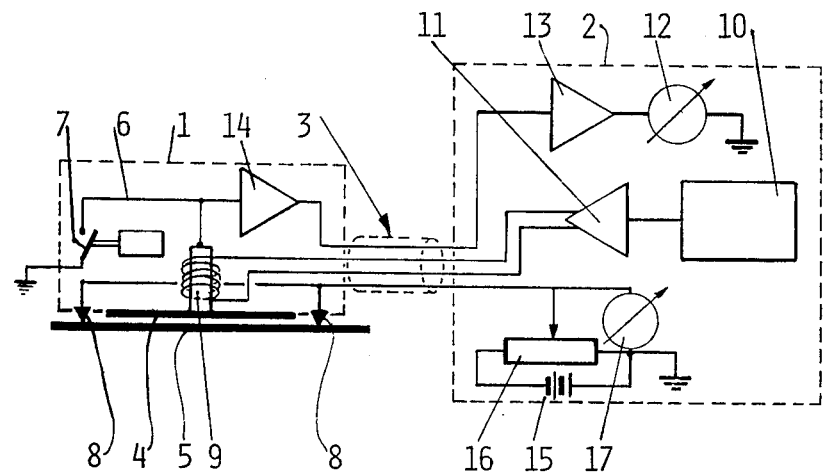
FIG. 1 shows schematically the various parts of the invented apparatus and the electric connections between those parts.

The main parts of the apparatus of FIG. 1 are a probe 1 and a measuring device 2 which have been interconnected by means of a flexible cable 3.

The probe 1 carries a plate 4 of conductive material, for instance gold or gold plated metal, and may be placed onto a metal surface 5 under examination in such a way that plate 4 extends at short distance parallel to that metal surface. An electric line 6 and a switch 7 will provide an electric connection between plate 4 and earth in such a way that plate 4 may be put on zero potential shortly prior to a measurement. During measurement, switch 7 is again in its open position shown in FIG. 1.

Coupled with plate 4 is an electric coil 9 which may cause the plate to vibrate in a direction vertical to the plane of capacitor 4,5. This coil 9 may be excited by a harmonic oscillator 10 via an amplifier 11 which parts are located in measuring apparatus 2.

A voltmeter 12 connected to line 6 via an electric line including two amplifiers 13,14, may serve for measuring the potential difference on the dynamic capacitor 4,5. In order to overcome the inconvenience of exactly adjusting the distance between plate 4 and metal surface 5 prior to each measurement a compensation circuit is present, this circuit comprising a D.C. source 15, a biassing resistance 16 and another voltmeter 17 which, on one hand, is grounded and, on the other hand, is connected via a line to contact points 8 of the probe still to be described. Parts 12, 13, 15, 16, 17 are located in the measuring apparatus 2 while the lines to the probe run through the connecting cable 3.

When this apparatus is in use, the probe is placed onto the surface 5 under examination, plate 4 being kept at the right distance from that surface by means of contact points 8 which serve as spacers. The contact points 8 also serve to apply an opposite potential derived from the compensation circuit, to metal surface 5. Subsequently, switch 7 is shut for a short time so as to bring plate 4 on ground potential. Via amplifier 11, oscillator 10 causes plate 4 to vibrate. Plate 4 and surface 5 then form a dynamic capacitor which emits a small potential to line 6, this potential being a measure for the electron escape energy. As a consequence thereof, voltmeter 12 shows a certain deflection. When the biassing resistance 16 of the compensation circuit is varied thereupon in such a way that the deflection of voltmeter 12 is reduced to 0, an equilibrium between the electron escape potential to be measured and the applied opposite potential will exist in line 6, and the value thereof may be read on voltmeter 17. This read-out value indicates the volta-potential of the system conductive plate-metal surface and constitutes a measure for the electron escape potential of the object under examination.

Figure 2:
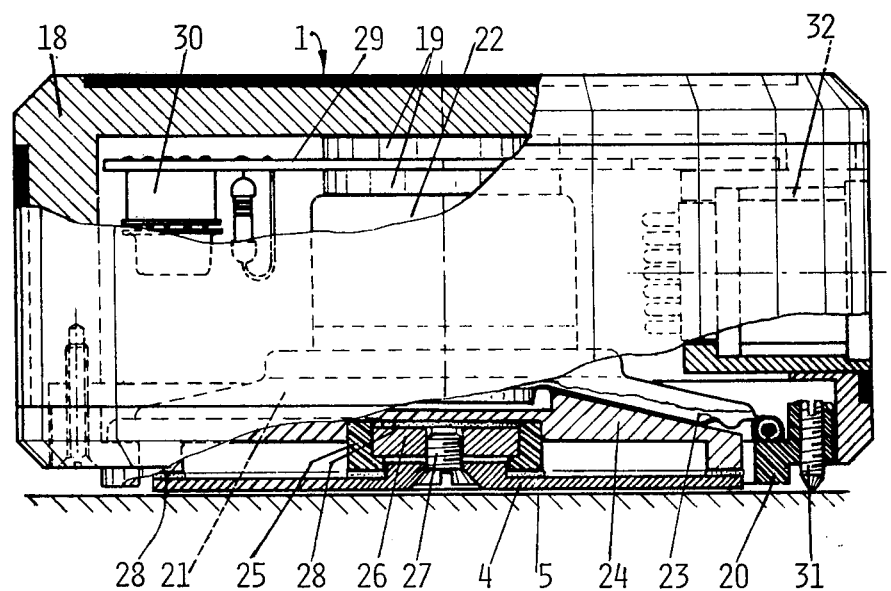
FIG. 2 shows the probe of the apparatus of FIG. 1 on a larger scale, partly in front and partly in cross-section.

FIG. 2 shows the actual construction of the probe. This probe 1 has a box-shaped metal housing 18 which is open on one side (in the drawing the bottom side). Plate 4 is located at this open side of the housing. A loudspeaker 21 is fitted in housing 18 by means of insulating rings 19,20 in such a way that the loudspeaker is both mechanically and electrically insulated with respect to the housing. Loudspeaker 21 is of the conventional type and comprises a coil 22 which upon excitation may cause a membrane 23 to vibrate. This coil 22 corresponds to coil 9 of FIG. 1. In loudspeaker 21, and in close contact with membrane 23, a metal disc 24 is mounted which bears the plate 4 via rings 25,26 and a screwed coupling 27. Due to this construction, the probe plate 4 may vibrate with membrane 23 as soon as coil 22 is excited. Plate 4 is electrically insulated from disc 24 by means of insulation material 28, and ring 25 is made of non-conductive material. Furthermore, a plate 28 with amplifier 30 and parts of the electric connection are fitted in housing 18 in such a way that they also are mechanically and electrically insulated with respect to that housing.

Between the circumferential rim of loudspeaker 21 and housing 18 there are moreover metal contact pins 31 which are electrically connected with housing 18 (three pins on the circumference of the housing) but insulated with respect to the loudspeaker. Through these pins, the probe rests on the metal surface 5 under examination, so that the pins act as spacers. At the same time, they also are the electric contact points with the metal surface and serve to apply the opposite potential derived from the compensation circuit onto that metal surface.

Of course, contact pins 31 alone might also provide electric contact, the extended rims of the housing then constituting the spacers. When the housing itself is kept at the opposite potential derived from the compensation circuit, no special contact pins need be used in that case.

The housing furthermore bears a plug contact 32 into which a plug of flexible cable 3 may be inserted. Electrical connections (not shown) run from this plug contact 32 to contact pins 31 (or housing 18), switch 7, coil 22 and amplifier 30.

Needless to say that numerous variations of the construction as shown are possible within the scope of the invention.

What I claim is:

1. In apparatus for measuring the electron escape potential of a metal surface which includes a conductive plate disposed is closely spaced parallel relation to a metal surface at which the electron escape potential is to be measured; means for vibrating said conductive plate in a direction vertical to said metal surface; circuit means connected to said conductive plate for measuring the potential difference between said metal surface and said conductive plate and including first mechanism for indicating such potential difference; the improvement which comprises:

external circuit means including a source of potential, divider means connected across said source of potential and including an adjustable tap connected to said metal surface, and second mechanism for indicating the potential difference between said tap and said source of potential; and switch means for temporarily connecting said conductive plate to said source of potential prior to measurement to charge the capacitor defined by said conductive plate and said metal surface;

said adjustable tap being adjusted during measurement to zero the indication of said first mechanism whereby said second mechanism directly indicates the electron escape potential of said metal surface independent of the precise spacing between said conductive plate and said metal surface.

2. The method of measuring the electron escape potential of a metal surface which comprises the steps of:
 (a) placing a conductive plate in closely spaced, parallel relation to a metal surface to define a capacitor;
 (b) connecting a reference potential to said conductive plate while connecting a different potential to said metal surface whereby to charge said capacitor;
 (c) removing the connection between said reference potential and said conductive plate;
 (d) vibrating said conductive plate perpendicular to said metal surface to generate an a.c. signal between said conductive plate and said metal surface;
 (e) adjusting the potential on said metal surface to null said a.c. signal generated in step (d); and
 (f) measuring the electron escape potential by measuring the adjusted potential to step (e) relative to said reference potential.

* * * * *